United States Patent [19]

Woodard et al.

[11] Patent Number: 5,674,997
[45] Date of Patent: *Oct. 7, 1997

[54] DNA PURIFICATION ON MODIFIED SILIGATES

[75] Inventors: Daniel Lee Woodard; Adriann Jeanelle Howard, both of Raleigh; James Arthur Down, Cary, all of N.C.

[73] Assignee: Becton Dickinson and Company, Franklin Lakes, N.J.

[*] Notice: The term of this patent shall not extend beyond the expiration date of Pat. No. 5,523,392.

[21] Appl. No.: 438,938

[22] Filed: May 10, 1995

Related U.S. Application Data

[62] Division of Ser. No. 127,403, Sep. 27, 1993, Pat. No. 5,503,816.

[51] Int. Cl.$^6$ .............................. C07H 1/06; C07H 1/08
[52] U.S. Cl. .............................. 536/25.4; 435/91.1
[58] Field of Search .............................. 536/25.3, 25.4

[56] References Cited

U.S. PATENT DOCUMENTS

| | | | |
|---|---|---|---|
| 5,342,931 | 8/1994 | Woodard et al. | 536/25.3 |
| 5,405,951 | 4/1995 | Woodard et al. | 536/25.3 |

FOREIGN PATENT DOCUMENTS

| | | |
|---|---|---|
| 0 268 946 A3 | 6/1988 | European Pat. Off. . |
| 0 442 026 A2 | 8/1991 | European Pat. Off. . |
| 0 540 170 A1 | 5/1993 | European Pat. Off. . |
| 0 600 253 A1 | 6/1994 | European Pat. Off. . |

*Primary Examiner*—Gary L. Kunz
*Attorney, Agent, or Firm*—David W. Highet, Esq.

[57] ABSTRACT

The present invention relates to a silicon-containing material which exhibits sufficient hydrophilicity and sufficient electropositivity to bind DNA from a suspension containing DNA and permit elution of the DNA from the material. Generally, the hydrophilic and electropositive characteristics are expressed at the surface of the silicon-containing material. Preferred silicon-containing materials of the present invention include boron silicate, aluminum silicate, phosphosilicate, silica carbonyl, silica sulfonyl and silica phosphonyl. The silicon-containing materials of the present invention are particularly useful in processes for purification of DNA from other cellular components. In these processes, a suspension of cellular components is placed in contact with the silicon-containing material, the silicon-containing material is washed to remove all cellular components other than DNA which are bound to the material, and the bound DNA is eluted from the material. Several of the silicon-containing materials are capable of binding and eluting DNA using only water.

3 Claims, No Drawings

DNA PURIFICATION ON MODIFIED SILIGATES

This is a division of application Ser. No. 08/127,403, filed Sep. 27, 1993, now U.S. Pat. No. 5,503,816.

BACKGROUND OF THE INVENTION

The present invention relates generally to the purification of DNA by solid phase extraction, and more specifically to silicon-containing materials which are capable of binding DNA and eluting DNA under suitable conditions.

The preparation of high-purity double-stranded (ds) plasmid DNA, single-stranded (ss) phage DNA, chromosomal DNA and agarose gel-purified DNA fragments is of critical importance in molecular biology. Ideally, a method for purifying DNA should be simple, rapid and require little, if any, additional sample manipulation. DNA rendered by such a method should be immediately amenable to transformation, restriction analysis, ligation or sequencing. A method with all of these features would be extremely attractive in the automation of DNA sample preparation, a goal of research and diagnostic laboratories. Typically, the preparation of plasmid DNA from crude alcohol precipitates is laborious, most often utilizing CsCl gradients, gel filtration, ion exchange chromatography, or RNase, proteinase K and repeated alcohol precipitation steps. These methods also require considerable downstream sample preparation to remove CsCl and other salts, ethidium bromide and alcohol. Similar arguments extend when using any of these methods for purifying DNA fragments. A further problem with these methods is that small, negatively-charged cellular components can co-purify with the DNA. Thus, the DNA can have an undesirable level of contamination.

DNA can also be purified using solid phases. Conventional solid phase extraction techniques have utilized surfaces which either (1) fail to attract and hold sufficient quantities of DNA molecules because of surface design to permit easy recovery of the DNA molecules during elution, or (2) excessively adhere DNA molecules to the surface, thereby hindering recovery of the DNA molecules during elution. Conventional surface materials which cause these problems when utilized in solid phase extraction include silica surfaces such as glass and Celite. Adequate binding of DNA to these types of surfaces can be achieved only by utilizing high concentrations of chaotropes or alcohols which are generally toxic, caustic, and/or expensive. For example, it is known that DNA will bind to crushed glass powders and to glass fiber filters in the presence of chaotropes. The chaotropic ions typically are washed away with alcohol, and the DNAs are eluted with low-salt solutions or water. Importantly, RNA and protein do not bind. However, a serious drawback in the use of crushed glass powder is that its binding capacity is low. In addition, glass powders often suffer from inconsistent recovery, incompatibility with borate buffers and a tendency to nick large DNAs. Similarly, glass fiber filters provide a nonporous surface with low DNA binding capacity. Other silicas, such as silica gel and glass beads, are not suitable for DNA binding and recovery. Currently, the solid phase of choice for solid phase extraction of DNA is Celite such as found in Prep-A-Gene™ by Bio-Rad Laboratories. As with the crushed glass powders, high concentrations of chaotropes are required for adequate binding of the DNA to the Celite.

SUMMARY OF THE INVENTION

These problems with conventional DNA purification methods are addressed by the present invention, which relates to a silicon-containing material which exhibits sufficient hydrophilicity and sufficient electropositivity to bind DNA from a suspension containing DNA and permit elution of the DNA from the material. Generally, the hydrophilic and electropositive characteristics are expressed at the surface of the silicon-containing material, and are quantified as the presence of oxygen as measured by Fourier transform infrared spectroscopy (FTIR) and the presence of the substituted atom as detected by electron surface composition analysis (ESCA). Preferred silicon-containing materials of the present invention include boron silicate, aluminum silicate, phosphosilicate, silica carbonyl, silica sulfonyl and silica phosphonyl.

The silicon-containing materials of the present invention are particularly useful in processes for purification of DNA from other cellular components. In these processes, a suspension of cellular components is placed in contact with the silicon-containing material, the silicon-containing material is washed to remove all cellular components other than DNA which are bound to the material, and the bound DNA is eluted from the material. Several of the silicon-containing materials are capable of binding and eluting DNA using only pure water, i.e., without the use of chaotropes.

DETAILED DESCRIPTION OF THE INVENTION

The present invention relates to a silicon-containing material which exhibits sufficient hydrophilicity and sufficient electropositivity to bind DNA from a suspension of cellular components and permit elution of the DNA from the material. It has been found that much lower concentrations of chaotropes or alcohols can be utilized to achieve purification of DNA using the instant silicon-containing materials.

DNA interacts with a solid phase surface in two ways. First, DNA interacts with the surface through hydrogen bonding between hydroxyl groups of DNA and surface components of the solid phase, such as surface hydroxyls. The second interaction is between the negatively charged phosphates of the DNA and positively charged elements of the solid phase surface. The hydrophilic and electropositive characteristics of the solid phase surface must be such as to allow binding of the DNA from a suspension of cellular components, a suspension of nucleic acid and other components, and/or a suspension of nucleic acid, and to permit elution of the DNA from the solid phase material. Thus, the electropositive characteristics of the solid phase material cannot have too high of a positive charge, or the DNA will stick to the surface and cannot be eluted. This characteristic is also true for many metal-based surfaces, which has resulted in their inability to be utilized for purification of DNA.

Silicon-containing materials, e.g., silica, Celite, glass powders and the like, have been used for DNA purification with mixed results. Some of these surfaces have low binding capacities and/or require the use of highly concentrated solutions of chaotropes or alcohols for the binding of DNA. Thus, it is desired to produce solid phase surfaces, particularly solid phases of silicon-containing materials, which exhibit suitable hydrophilic and electropositive characteristics for DNA purification and/or for DNA purification with much lower concentrations of chaotropes or alcohols. On the surface of the solid phase, hydrophilic characteristics are achieved by the presence of groups that will attract water molecules. Suitable groups include —OH, —NH, —F, —H or groups with double-bonded oxygen such as carbonyl, sulfonyl or phosphonyl. Electropositive characteristics are achieved by the presence of positively charged atoms. Suitable positively-charged atoms include Si, B or Al. In accordance with the present invention, silicon-containing materials are prepared in which the hydrophilic characteristics are achieved by incorporation of the appropriate hydrophilic groups, and the electropositive characteristics are achieved by incorporation of Si and other appropriate positively-charged atoms. Preferred silicon-containing materials of the present invention include boron silicates, aluminum silicates, phosphosilicates, silica carbonyl, silica sulfonyl and silica phosphonyl.

In general, the silicon-containing materials of the present invention are prepared by reacting $SiCl_4$ with $RCl_n$ and $H_2O$ at about 0° to 10° C., preferably 0° to 5° C., most preferably 0° C., wherein R may be B, Al P, CO, PO or SO, and n may be 2 or 3, to complete the valency of R. For example, n is 2 for R=CO or SO, and n is 3 for B, Al, P or PO. Silicon-containing materials are prepared with different ratios of R:Si by reacting different proportions of $SiCl_4$ and $RCl_n$. In general, $RCl_n$ and $SiCl_4$ are mixed together and cooled. Water is slowly added until gas no longer evolves. Extra water is added to ensure a complete reaction. The silicon-containing material is filtered, washed, dried briefly and stored in a desiccator.

Silicon-containing materials containing boron (i.e., boron silicates) are prepared as generally described above. The boron atom is less electropositive than the silicon atom. The presence of boron causes DNA to bind or stick under binding conditions. However, since boron is less electropositive than silicon, the bound DNA would elute much more easily from the boron silicate during the elution step. Boron silicates have been prepared by reacting $SiCl_4$ with between about 0.09 to about 5 equivalents of $BCl_3$. In general, as the percentage of boron in the surface of the boron silicates increases, the recovery of DNA from that surface also increases and the lower molarity of binding agent (e.g., chaotrope) can be used to achieve these results. Boron silicates prepared by reacting $SiCl_4$ with about 0.09 to about 1.5 equivalents of $BCl_3$ were found to provide good recovery of DNA from biological samples, even at low concentrations of binding agent. It is preferred that the boron silicates be prepared by reacting $SiCl_4$ with about 0.3 to about 1.0 equivalent of $BCl_3$, and most preferred that they be prepared by reacting $SiCl_4$ with about 0.3 to about 0.9 equivalent of $BCl_3$. For DNA recovery, many of these boron silicates out-perform super fine super floss Celite.

Aluminum silicates are prepared as generally described above. Since the aluminum atom is more electropositive than the silicon atom, less aluminum should be present in the aluminum silicates than boron was present in the boron silicates, to assure recovery of bound DNA. The presence of aluminum causes DNA to bind more tightly under binding conditions. Aluminum silicates have been prepared by reacting $SiCl_4$ with about 0.05 to about 3 equivalents of $AlCl_3$. In general, as the percentage of aluminum in the surface of the aluminum silicates increases, the recovery of DNA from the surface decreases. Aluminum silicates prepared by reacting $SiCl_4$ with about 0.05 to about 0.5 equivalent of $AlCl_3$ were found to provide good recovery of DNA even at low concentrations of binding agent (e.g., chaotrope). It is preferred that the aluminum silicates be prepared by reacting $SiCl_4$ with about 0.05 to about 0.3 equivalent of $AlCl_3$, and most preferred that they be prepared by reacting $SiCl_4$ with about 0.05 to about 0.15 equivalent of $AlCl_3$.

Aluminum silicates prepared by reacting $SiCl_4$ with more than 0.5 to about 3 equivalents of $AlCl_3$ irreversibly bind DNA and can thus be used to remove DNA contaminants from biological samples for in vitro diagnostics or can be used to immobilize DNA for purposes of detection.

Phosphosilicates are prepared as generally described above. The phosphorous atom is less electro-positive than the boron atom. The phosphosilicates have DNA binding capacities similar to those of the boron silicates, although not as striking. Phosphosilicates have been prepared by reacting $SiCl_4$ with about 0.1 to about 5 equivalents of $PCl_3$. In general, as the percentage of phosphorus in the surface of the silicates increases, the recovery of DNA from the surface also increases. Phosphosilicates prepared by reacting $SiCl_4$ with about 0.1 to about 5 equivalents of $PCl_3$ were found to provide good recovery of DNA even at a low concentration of binding agent (e.g., chaotrope). It is preferred that the phosphosilicates be prepared by reacting $SiCl_4$ with about 0.3 to about 5 equivalents of $PCl_3$, and most preferred that they be prepared by reacting $SiCl_4$ with about 1 to about 5 equivalents of $PCl_3$.

Silica carbonyls are prepared as generally described above. The carbon atom is less electropositive than the boron or phosphorus atom. The silica carbonyls have DNA binding capacities similar to those of the boron silicates, although at a higher percentage of carbonyl to silicon. Silica carbonyls have been prepared by reacting $SiCl_4$ with about 0.1 to about 1.5 equivalents of $COCl_2$. In general, as the percentage of carbonyl in the surface of the silica carbonyls increases, the recovery of DNA from the surface also increases. Silica carbonyls prepared by reacting $SiCl_4$ with about 0.1 to about 1.5 equivalents of $COCl_2$ were found to provide good recovery of DNA even at low concentrations of binding agent (e.g., chaotrope). It is preferred that the silica carbonyls be prepared by reacting $SiCl_4$ with about 0.1 to about 0.4 equivalent of $COCl_2$, and most preferred that they be prepared by reacting $SiCl_4$ with about 0.25 to about 0.35 equivalent of $COCl_2$. For DNA recovery, many of these silica carbonyls out-perform super fine super floss Celite.

Silica sulfonyls are prepared as generally described above. The sulfur atom has electropositive characteristics similar to those of the carbon atom. The silica sulfonyls have similar, although better, binding capabilities to those of the silica carbonyls. Silica sulfonyls have been prepared by reacting $SiCl_4$ with about 0.1 to about 1.5 equivalents of $SOCl_2$. In general, as the percentage of sulfonyl in the surface of the silica sulfonyls increases, the recovery of DNA from the surface also increases. Silica sulfonyls prepared by reacting $SiCl_4$ with about 0.1 to about 1.5 equivalents of $SOCl_2$ were found to provide good recovery of DNA even at low concentrations of binding agent (e.g., chaotrope). It is preferred that the silica sulfonyls be prepared by reacting $SiCl_4$ with about 0.3 to about 1.5 equivalents of $SOCl_2$, and most preferred that they be prepared by reacting $SiCl_4$ with about 0.7 to about 1.5 equivalents of $SOCl_2$. For DNA recovery, many of these silica sulfonyls out-perform super fine super floss Celite. For DNA recovery, the silica sulfonyls generally are superior to the other silicon-containing materials of the present invention.

Silica phosphonyls are prepared as generally described above. The phosphorous atom is less electro-positive than the boron atom, but more electropositive than the carbon or sulfur atoms. Hydrophilic characteristics are imparted to the surface by the oxygen of the phosphonyl. The silica phosphonyls have binding characteristics similar to those of the silica carbonyls. The presence of phosphorous causes DNA to bind more tightly under binding conditions than in the silica carbonyls or silica sulfonyls. Silica phosphonyls have been prepared by reacting $SiCl_4$ with about 0.1 to about 2.0 equivalents of $POCl_3$. In general, as the percentage of phosphonyl in the surface of the silica phosphonyls increases, the recovery of DNA from the surface also increases. Silica phosphonyls prepared by reacting $SiCl_4$ with about 0.1 to about 2 equivalents of $POCl_3$ were found to provide good recovery of DNA even at low concentrations of binding agent (e.g., chaotrope). It is preferred that the silica phosphonyls be prepared by reacting $SiCl_4$ with about 0.3 to about 2 equivalents of $POCl_3$, and most preferred that they be prepared by reacting $SiCl_4$ with about 0.5 to about 1 equivalent of $POCl_3$.

The silicon-containing materials of the present invention are used for purification of DNA from other cellular components or potential contaminants. In either instance, the DNA can be obtained from any source, including but not limited to crude cell extracts, biological fluids, phage supernatants, agarose gels and radiolabelling reactions. Alternatively, the aluminum silicates prepared by reacting $SiCl_4$ with more than 0.5 equivalent of $AlCl_3$ can be used to immobilize DNA. The DNA can be double-stranded, single-stranded, circular or linear, and can be variable in size. Conventional techniques for obtaining DNA from any source, well known in the art, are utilized to prepare the DNA for purification. Typical procedures for obtaining DNA end with a suspension of the DNA in solution. For isolation of DNA from biological samples, see, e.g., Harding, J. D. et al., *Nucleic Acids Research* 17:6947 (1989) and Marko, M. A. et al., *Analytical Biochemistry* 121:382 (1982). Procedures for isolation of plasmid DNA can be found in Lutze, L. H. et al., *Nucleic Acids Research* 20:6150 (1990). Extraction of double-stranded DNA from biological samples can be found in Yamada, O. et al., *Journal of Virological Methods* 27:203 (1990). Most DNA solutions comprise the DNA in a suitable buffer such as TE (Tris-EDTA), TEA (40 mm Tris-acetate, 1 mm EDTA) buffer, or a lysate. See also Sambrook, J. et al., *Molecular Cloning: A Laboratory Manual*, 2nd Ed., Cold Spring Harbor Laboratory Press, New York (1989).

Once the DNA is obtained in a suitable solution or suspension, the silicon-containing material of the present invention is added to the solution or suspension. Alternatively, the DNA solution or suspension could be added to the silicon-containing material of the present invention. After the DNA solution or suspension is contacted with the silicon-containing material of the present invention, a binding buffer typically is added to assist in the binding of the DNA to the silicon-containing material. Suitable binding buffers include well-known chaotropes such as $NaClO_4$ and NaI, and other agents such as isopropanol, NaCl or guanidine HCl. After the DNA is bound to the silicon-containing material, the pure DNA is eluted from the silicon-containing material. Suitable eluting agents include 10 mM Tris, pH 7.0 or water. Generally, the silicon-containing material with bound DNA is separated, e.g., by centrifugation or filtration, and washed prior to eluting the DNA. Suitable washing agents include 80/20 ethanol/50 mM Tris, pH 7.0, and other low molecular weight alcohols.

It has further been discovered that many of the silicon-containing materials described above are capable of binding DNA in pure water at room temperature, thus eliminating the use of chaotropic binding buffers. The bound DNA is eluted in pure water at 37° C. The elimination of the chaotropic binding buffers is a significant advance in the technology.

The DNA obtained by purification with the silicon-containing materials of the present invention may be used without further manipulation for restriction enzyme digestion, cloning, sequencing, diagnostics and the like. The high quality of DNA prepared with the present invention and the speed with which DNA is purified with minimal downstream processing mean that these silicon-containing materials can be useful in the automation of DNA sample preparation.

The irreversible binding of DNA to some of the aluminum silicates is useful to remove DNA contaminants from biological samples for in vitro diagnostics or to immobilize DNA for purposes of detection.

The present invention is described by reference to the following Examples, which are offered by way of illustration and are not intended to limit the invention in any manner. Standard techniques well known in the art or the techniques specifically described below were utilized.

EXAMPLE 1

Synthesis of Silicon-Containing Materials

A. Boron Silicates

Boron silicates prepared by reacting $SiCl_4$ with 0.1 to 5 equivalents of $BCl_3$ were prepared using the following ratios of $BCl_3$ (1M in $CH_2Cl_2$; Aldrich Chemical Co.) and $SiCl_4$ (Petrach Systems):

|     | $BCl_3$ |      | $SiCl_4$ |      |
| --- | ---     | ---  | ---      | ---  |
| Rxn | ml      | mMol | ml       | mMol |
| 1   | 1       | 1    | 1.34     | 10   |
| 2   | 2       | 2    | 1.34     | 10   |
| 3   | 5       | 5    | 1.34     | 10   |
| 4   | 7       | 7    | 1.34     | 10   |
| 5   | 10      | 10   | 1.34     | 10   |
| 6   | 5       | 5    | .134     | 1    |
| 7   | 5       | 5    | .268     | 2    |
| 8   | 5       | 5    | .402     | 3    |
| 9   | 5       | 5    | .536     | 4    |
| 10  | 5       | 5    | 0.000    | 0    |

The $SiCl_4$ and $BCl_3$ were mixed with stirring and cooled to 0° C. in ice. Water was slowly added until HCl gas was longer evolved from the reaction vessel. About 5 ml of water was then added to ensure a complete reaction. The reaction mix was stirred for one hour and filtered, washed three times in 10 ml $H_2O$ and three times in 10 ml acetone. The boron silicate was air-dried for minutes and then dried at 100° C. for one hour. The boron silicate was stored in a desiccator until used.

B. Aluminum Silicates

Aluminum silicates prepared by reacting $SiCl_4$ with 0.1 to 3 equivalents of $AlCl_3$ were prepared using the following ratios of $AlCl_3$ (1M in nitrobenzene; Aldrich Chemical Co.) and $SiCl_4$ (Petrach Systems):

|     | $AlCl_3$ |      | $SiCl_4$ |      |
| --- | ---      | ---  | ---      | ---  |
| Rxn | ml       | mMol | ml       | mMol |
| 1   | 1        | 1    | 1.34     | 10   |
| 2   | 3        | 3    | 1.34     | 10   |
| 3   | 5        | 5    | 1.34     | 10   |
| 4   | 7        | 7    | 1.34     | 10   |
| 5   | 10       | 10   | 1.34     | 10   |
| 6   | 7.5      | 7.5  | 0.67     | 5    |
| 7   | 10       | 10   | 0.67     | 5    |
| 8   | 15       | 15   | 0.67     | 5    |

The $SiCl_4$ and $AlCl_3$ were mixed together and cooled in an ice bath for 15 minutes. Water was added dropwise very slowly (5 drop/2 min.) with vigorous stirring until HCl gas no longer evolved from the reaction vessel. About 3 ml of water was then added to ensure a complete reaction. The reaction mixture was stirred at room temperature for 15 minutes and filtered. The aluminum silicate was washed three times with 70 ml acetone, three times with water, and three times with acetone. The washed aluminum silicate was air-dried for 20 minutes, oven-dried one hour at 100° C., and stored in a desiccator until used.

C. Phosphosilicates

Phosphosilicates prepared by reacting $SiCl_4$ with 0.1 to 5 equivalents of $PCl_3$ were prepared using the following ratios of $PCl_3$ (2M in $CH_2Cl_2$; Aldrich Chemical Co.) and $SiCl_4$ (Petrarch Systems):

|     | $PCl_3$ | | | $SiCl_4$ | |
| --- | --- | --- | --- | --- | --- |
| Rxn | eq. | ml | mMol | ml | mMol |
| 1 | .1 | .5 | 1 | 1.34 | 10 |
| 2 | .3 | 1.5 | 3 | 1.34 | 10 |
| 3 | .5 | 2.5 | 5 | 1.34 | 10 |
| 4 | .7 | 3.5 | 7 | 1.34 | 10 |
| 5 | 1 | 5.0 | 10 | 1.34 | 10 |
| 6 | 1.5 | 3.75 | 7.5 | 0.65 | 5 |
| 7 | 2 | 5.0 | 10 | 0.65 | 5 |
| 8 | 3 | 7.5 | 15 | 0.65 | 5 |
| 9 | 4 | 10.0 | 20 | 0.65 | 5 |
| 10 | 5 | 12.5 | 25 | 0.65 | 5 |

The $SiCl_4$ was added to 25 ml Erlenmeyer flask and cooled to 0° C. in an ice bath for about 10 minutes. The $PCl_3$ was then added and the mixture cooled for five minutes. Water was added dropwise very slowly (about 2 drops/min) until white gas was no long evolved following the addition of the water. The reaction mixture was stirred for five minutes, and 3 ml water added in 1 ml increments to ensure a complete reaction. The reaction mixture was stirred at room temperature for 15 minutes and filtered. The phosphosilicate was washed three times with water and three times with acetone. The washed phosphosilicate was then air-dried for 15 minutes, oven-dried one hour at 100° C., and stored in a desiccator until used.

D. Silica Carbonyls

Silica carbonyls prepared by reacting $SiCl_4$ with 0.1 to 1.5 equivalents of $COCl_2$ were prepared using the following ratios of phosgene (Fluka) and $SiCl_4$ (Petrarch Systems):

|     | Phosgene | | $SiCl_4$ | |
| --- | --- | --- | --- | --- |
| Rxn | ml | mMol | ml | mMol |
| 1 | .52 | 1 | 1.34 | 10 |
| 2 | 1.56 | 3 | 1.34 | 10 |
| 3 | 2.60 | 5 | 1.34 | 10 |
| 4 | 3.64 | 7 | 1.34 | 10 |
| 5 | 5.20 | 10 | 1.34 | 10 |
| 6 | 7.80 | 15 | 1.34 | 10 |

The phosgene and $SiCl_4$ were mixed together and cooled to 0° C. in an ice bath for 10 minutes. Water was added incrementally (10 drops/2 min) to keep the reaction mixture from getting too hot. After a total of 3 ml of water was added, the reaction mixture was stirred at 0° C. for 10 minutes and then at room temperature for one hour to get rid of any unreacted phosgene. The reaction mixture was filtered in a Buchner funnel. The silica carbonyl was washed three times with 10 ml of water and three times with 10 ml acetone, air-dried one hour, oven-dried one hour at 100° C., and stored in a desiccator.

E. Silica Sulfonyls

Silica sulfonyls prepared by reacting $SiCl_4$ with 0.1 to 1.5 equivalents of $SOCl_2$ were prepared using the following ratios of thionyl chloride (Aldrich Chemical Co.) and $SiCl_4$ (Petrarch Systems):

|     | Thionyl Chloride | | $SiCl_4$ | |
| --- | --- | --- | --- | --- |
| Rxn | ml | mMol | ml | mMol |
| 1 | .074 | 1 | 1.34 | 10 |
| 2 | .222 | 3 | 1.34 | 10 |
| 3 | .370 | 5 | 1.34 | 10 |
| 4 | .518 | 7 | 1.34 | 10 |
| 5 | .740 | 10 | 1.34 | 10 |
| 6 | 1.110 | 15 | 1.34 | 10 |

The $SiCl_4$ and thionyl chloride were added to a 25 ml Erlenmeyer flask and cooled to 0° C. with stirring in a wet ice bath. Ten drops of water were added and the mixture stirred for two minutes. Five drops of water were then added every two minutes, with continuous stirring until the gas no longer evolved. Two ml water was then added to ensure a complete reaction. The reactive mixture was stirred at room temperature for one hour, and filtered and washed three times with 10 ml water and three times with 10 ml acetone. The silica sulfonyl was air-dried for one hour, oven-dried for one hour at 100° C., and stored in a desiccator.

F. Silica Phosphonyls

Silica phosphonyls prepared by reacting $SiCl_4$ with 0.1 to 2.0 equivalents of $POCl_3$ were prepared using the following ratios of $POCl_3$ (Aldrich Chemical Co.) and $SiCl_4$ (Petrarch Systems):

|     | $POCl_3$ | | | $SiCl_4$ | |
| --- | --- | --- | --- | --- | --- |
| Rxn | eq. | ml | mMol | ml | mMol |
| 1 | .1 | 0.9 | 1 | 1.34 | 10 |
| 2 | .3 | .28 | 3 | 1.34 | 10 |
| 3 | .5 | .46 | 5 | 1.34 | 10 |
| 4 | .7 | .63 | 7 | 1.34 | 10 |
| 5 | 1 | .93 | 10 | 1.34 | 10 |
| 6 | 1.5 | .70 | 7.5 | 0.67 | 5 |
| 7 | 2 | 1.86 | 20 | 1.34 | 10 |

The $SiCl_4$ was added to 25 ml Erlenmeyer flask and cooled to 0° C. in an ice bath for about 10 minutes. The $POCl_3$ was then added via syringe and the mixture was cooled for five minutes. Water was added dropwise very slowly (about 2 drops/min) with vigorous stirring until visible signs of reaction subsided (no white gas evolved, or bubbling). The reaction mixture was stirred at 0° C. for 5–10 minutes. About 5 ml water was added in 1 ml increments to ensure a complete reaction. The reaction mixture was then stirred at room temperature for 15 minutes and filtered. The silica phosphonyl was washed three times with 10 ml water and three times with 10 ml acetone. The washed silica phosphonyl was then air-dried for 15 minutes, oven-dried for one hour at 100° C., and stored in a desiccator until used.

EXAMPLE 2

Analysis of DNA Recovery Using Super Fine Super Floss Celite as Standard

The following materials were utilized for the analysis of DNA recovery with super fine super floss Celite as a standard for the analysis of the DNA recovery capabilities of the silicon-containing materials:

Super Fine Super Floss Celite (Manville; 1:5 w/w in $H_2O$) [SFSF]

λ DNA (BRL Cat. No. 56125A)

50 mM Tris, pH 7.0 (diluted from 1M stock)

Binding buffers ($H_2O$ or $NaClO_4$ diluted from 6M stock)

80% ethanol in 50 mM Tris, pH 7.0

MilliQ $H_2O$

Ethidium bromide (10 mg/ml)

1% agarose

1× TAE (diluted from 50× stock)

Type II loading dye (25% Ficoll 400, 25% bromophenol blue, 25% xylene cyanol)

Types 57 and 55 Polaroid film

Fifty µl of λ DNA solution (0.5 µl λ DNA in 50 µl 50 mM Tris, pH 7.0, for 31 µg DNA/reaction) were added to eight tubes. Twenty µl of SFSF (~30 µg) was added to the DNA. Four hundred µl of binding buffer was added to the DNA as follows: $H_2O$ to tube 1; 1.0, 1.5, 2, 2.5, 3, 3.5 and 4M $NaClO_4$ to tubes 2–8, respectively. The mixture was incubated with rocking for 10 minutes at room temperature. The tubes were centrifuged and the supernatant was discarded. The resulting pellets were washed two times with 80/20 ethanol/50 mM Tris, pH 7.0. The DNA was eluted from the pellet in 20 µl water for 10 minutes at 37° C. The tubes were centrifuged and the supernatants of each saved in a separate tube. The pellets were eluted again, as before, the tubes centrifuged and the supernatants combined. Two µl of Type II loading dye was added to each tube of the supernatants and the mixture loaded into a 1% agarose, 1× TAE gel. The gel was run for about 25 minutes at 100–130 volts in 1× TAE buffer. The gels were stained with ethidium bromide in $H_2O$ (~1:1000) for ~20–30 minutes. Photographs over UV light were taken with Type 57 film and negatives were taken (when possible) with Type 55 film.

The gels showed that a small amount of DNA eluted from the SFSF with water used as the binding buffer. A small amount of DNA was also eluted with 1, 1.5 and 2.0M $NaClO_4$ used as the binding buffer. A dramatic rise in the amount of eluted DNA was seen with 2.5, 3.0, 3.5 and 4.0M $NaClO_4$ used as the binding buffer. When SFSF was compared with Prep-A-Gene™, it was seen that no DNA was eluted from the Celite of Prep-A-Gene™ until 3.0M $NaClO_4$ was used as the binding buffer, whereas SFSF bound some DNA in its native state and bound it more strongly at 2.5M $NaClO_4$. Thus, SFSF performed better than Prep-A-Gene™. In the Examples which follow, SFSF was used as the standard, using 3M $NaClO_4$ as the binding buffer.

EXAMPLE 3

Analysis of DNA Recovery Using Boron Silicates

The recovery of DNA using the boron silicates prepared in Example 1 was analyzed by following the procedure set forth in Example 2, except that seven tubes contained the boron silicate (~30 µg) and 1, 1.5, 2, 2.5, 3, 3.5 and 4M $NaClO_4$ was used as the binding buffer. The eighth tube (control) contained SFSF (~30 µg) and used 3.0M $NaClO_4$ as the binding buffer. The following results were obtained. A boron silicate prepared by reacting $SiCl_4$ with 0.09 equivalent of $BCl_3$ showed good recovery of DNA. A boron silicate prepared by reacting $SiCl_4$ with 0.16 equivalent of $BCl_3$ did not bind or elute any DNA under the conditions utilized. Since the product made with 0.09 equivalent gave good recovery, as did one made with 0.33 equivalent, $BCl_3$ (see below), this latter product is an example of a sporadic failure. A boron silicate prepared by reacting $SiCl_4$ with 0.55 equivalent of $BCl_3$ retained and eluted practically all of the DNA present. This boron silicate showed good recovery of DNA down to 1M $NaClO_4$ (i.e., 1M $NaClO_4$ used as binding buffer), retaining and eluting all DNA at this level. A boron silicate prepared by reacting $SiCl_4$ with 0.33 equivalent of $BCl_3$ gave excellent recovery of DNA (i.e., binding and eluting of DNA) down to 1.5M $NaClO_4$. A boron silicate prepared by reacting $SiCl_4$ with 0.42 equivalent of $BCl_3$ gave excellent recovery of DNA down to 2.0M $NaClO_4$.

EXAMPLE 4

Analysis of DNAS Recovery Using Aluminum Silicates

The recovery of DNA using aluminum silicates prepared in Example 1 was analyzed as described in Example 3. The following results were obtained. An aluminum silicate prepared by reacting $SiCl_4$ with 0.5 equivalent of $AlCl_3$ gave good recovery of DNA which remained chelated to small surface particles and stuck at the top of the gel. An aluminum silicate prepared by reacting $SiCl_4$ with 0.1 equivalent of $AlCl_3$ gave good recovery of DNA down to 2M $NaClO_4$ without any chelation problem. An aluminum silicate prepared by reacting $SiCl_4$ with 0.3 equivalent of $AlCl_3$ also showed the chelation problem seen with the reaction with 0.5 equivalent of $AlCl_3$. Aluminum silicates prepared by reacting $SiCl_4$ with 0.7, 1.0 or 1.5 equivalents of $AlCl_3$ bound but did not elute any DNA.

EXAMPLE 5

Analysis of DNA Recovery Using Phosphosilicates

The recovery of DNA using phosphosilicates prepared in Example 1 was analyzed as described in Example 3. The following results were obtained. A phosphosilicate prepared by reacting $SiCl_4$ with 0.1 equivalent of $PCl_3$ gave little but some recovery of DNA up to 4M $NaClO_4$. A phosphosilicate prepared by reacting $SiCl_4$ with 0.3, 0.5, 0.7 or 2.0 equivalents of $PCl_3$ gave good recovery of DNA down to 1M $NaClO_4$. A phosphosilicate prepared by reacting $SiCl_4$ with 1.0, 1.5, 3.0, 4.0 or 5.0 equivalents of $PCl_3$ gave excellent recovery of DNA.

EXAMPLE 6

Analysis of DNA Recovery Using Silica Carbonyls

The recovery of DNA using the silica carbonyls prepared in Example 1 was analyzed as described in Example 3. The following results were obtained. A silica carbonyl prepared by reacting $SiCl_4$ with 0.1 or 0.5 equivalent of $COCl_2$ gave good recovery of DNA down to 1M $NaClO_4$. A silica carbonyl prepared by reacting $SiCl_4$ with 1.0 equivalent of $COCl_2$ gave very good recovery of DNA down to 1M $NaClO_4$. A silica carbonyl prepared by reacting $SiCl_4$ with 0.3 equivalent of $COCl_2$ gave excellent recovery of DNA down to 2M $NaClO_4$.

EXAMPLE 7

Analysis of DNA Recovery Using Silica Sulfonyls

The recovery of DNA using the silica sulfonyls prepared in Example 1 was analyzed as described in Example 3. The following results were obtained. A silica sulfonyl prepared by reacting $SiCl_4$ with 0.1 equivalent of $SOCl_2$ gave good recovery of DNA down to 2M NaCl$_2$. A silicon sulfonyl prepared by reacting SiCl$_4$ with 0.70, 1.0 or 1.5 equivalents of SOCl$_2$ gave very good recovery of DNA down to 1M, 1.5M or 1M NaClO$_4$, respectively. A silica sulfonyl prepared by reacting SiCl$_4$ with 0.333 or 0.500 equivalents of SOCl$_2$ gave excellent recovery of DNA down to 1.5M or 2M NaClO$_4$, respectively.

EXAMPLE 8

Analysis of DNA Recovery Using Silica Phosphonyls

The recovery of DNA using the silica phosphonyls prepared in Example 1 was analyzed as described in Example 3. The following results were obtained. Silica phosphonyls prepared by reacting SiCl$_4$ with 0.1, 0.3, 1.5 or 2.0 equivalents of POCl$_3$ gave good recovery of DNA. Silica phosphonyls prepared by reacting SiCl$_4$ with 0.5, 0.7 or 1 equivalent of POCl$_3$ gave excellent DNA recovery.

EXAMPLE 9

Analysis of DNA Recovery Without Use of Chaotropes

The compounds that gave complete recovery of DNA down to 1M NaClO$_4$ were then tested for their ability to recover DNA in the absence of any binding buffer. DNA was bound to the silicon-containing material using pure water at room temperature. The bound DNA was eluted at 37° C. in pure water. The following silicon-containing materials were found to bind and elute DNA under these conditions:

Boron silicates prepared by reacting SiCl$_4$ with 0.3 or 0.8 equivalent of BCl$_3$;

Aluminum silicate prepared by reacting SiCl$_4$ with 0.1 equivalent AlCl$_3$;

Phosphosilicates prepared by reacting SiCl$_4$ with 1, 1.5, 3, 4 or 5 equivalents of PCl$_3$; and Silica phosphonyls prepared by reacting SiCl$_4$ with 0.5, 0.7 or 1.0 equivalent of POCl$_3$.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

What is claimed is:

1. A method for purifying DNA comprising the steps of:

(a) contacting a suspension containing DNA with a silicon-containing material which exhibits sufficient hydrophilicity and sufficient electropositivity to bind DNA from a suspension containing DNA and permit elution of the DNA from the material with water, said silicon-containing material selected from the group consisting of boron silicate prepared by reacting SiCl$_4$ with about 0.09 to about 1.5 equivalents of BCl$_3$ in the presence of water, aluminum silicate prepared by reacting SiCl$_4$ with about 0.1 to about 0.5 equivalents of AlCl$_3$ in the presence of water, phosphosilicate prepared by reacting SiCl$_4$ with about 0.1 to about 5 equivalents of PCl$_3$ in the presence of water, silica carbonyl prepared by reacting SiCl$_4$ with about 0.1 to about 1.5 equivalents of COCl$_2$ in the presence of water, silica sulfonyl prepared by reacting SiCl$_4$ with about 0.1 to about 1.5 equivalents of SOCl$_2$ in the presence of water, and silica phosphonyl prepared by reacting SiCl$_4$ with about 0.1 to about 2 equivalents of POCl$_3$ in the presence of water under conditions suitable to bind DNA to said material;

(b) washing said material having bound DNA; and (c) eluting the bound DNA from said material.

2. The method of claim 1 wherein the silicon-containing material is a phosphosilicate prepared by reacting SiCl$_4$ with about 0.1 to about 5 equivalents of PCl$_3$ in the presence of water.

3. The method of claim 1 wherein the silicon-containing material is a phosphosilicate prepared by reacting SiCl$_4$ with about 1 to about 5 equivalents of PCl$_3$ in the presence of water.

* * * * *